United States Patent [19]

Yamamoto et al.

[11] Patent Number: 5,395,943
[45] Date of Patent: Mar. 7, 1995

[54] METHOD FOR PURIFICATION OF 2-ALKYL-4-HALO-5-FORMYLIMIDAZOLES

[75] Inventors: Toshio Yamamoto; Yoshihiro Hibi; Toshimi Ogawa, all of Ogaki, Japan

[73] Assignee: Nippon Gohsei Kagaku Kogyo Kabushiki Kaisha, Osaka, Japan

[21] Appl. No.: 197,171

[22] Filed: Feb. 16, 1994

[51] Int. Cl.$^6$ ............................................. C07D 233/68
[52] U.S. Cl. .................................................. 548/333.5
[58] Field of Search ...................................... 548/333.5

[56] References Cited

U.S. PATENT DOCUMENTS

| | | | |
|---|---|---|---|
| 5,319,094 | 6/1994 | Kakimoto et al. | 548/341.5 |
| 5,336,779 | 8/1994 | Yamamoto et al. | 548/333.5 |

FOREIGN PATENT DOCUMENTS

| | | | |
|---|---|---|---|
| 243076 | 10/1988 | Japan | 548/333.5 |
| 2267605A | 12/1993 | United Kingdom . | |

*Primary Examiner*—Mary C. Lee
*Assistant Examiner*—Jacqueline Haley
*Attorney, Agent, or Firm*—Armstrong, Westerman, Hattori, McLeland & Naughton

[57] ABSTRACT

The invention provides a method of purifying 2-alkyl-4-halo-5-formylimidazoles, which comprises dissolving an 2-alkyl-4-halo-5-formylimidazole in an aqueous solution of a sulfonating agent, adjusting the solution to pH 1-6, and removing the impurity 2-alkyl-4,5-dihaloimidazole by filtration or extraction.

4 Claims, No Drawings

METHOD FOR PURIFICATION OF 2-ALKYL-4-HALO-5-FORMYLIMIDAZOLES

FIELD OF THE INVENTION

This invention relates to a method of purifying 2-alkyl-4-halo-5-formylimidazoles which are of value as starting compounds for the production of diuretics, antihypertensive drugs and other medicinally active substances.

BACKGROUND OF THE INVENTION

2-Alkyl-4-halo-5-formylimidazoles find application as starting materials for the production of drugs, such as diuretics, antihypertensive drugs, etc. and, as such, are attracting much attention but there is little literature on the methodology for their production. Thus, all that is known is the method starting with 2-amino-3,3-dichloroacrylonitrile and an aldehyde and involving the formation of a Schiff base (cf. Japanese Patent Application Kokai No. 148788/1979).

However, this method was found to be not satisfactory in that the starting compound 2-amino-3,3-dichloroacrylonitrile was not easily available, thus being a serious deterrent to commercial scale production. Therefore, the development of a new production process for 2-alkyl-4-halo-5-formylimidazoles was awaited in earnest by the industry.

Under the circumstances the inventors of this invention discovered a new production process comprising halogenating 2-alkyl-5-formylimidazoles with an N-halosuccinimide to give 2-alkyl-4-halo-5-formylimidazoles and filed a Japanese patent application No. 18717/1991 (Japanese Patent Application Kokai No. 327575/1992) and the corresponding U.S. patent application (U.S. application Ser. No. 07/999,134 (CIP Application). Incidentally, regarding the process for producing 2-alkyl-5-formylimidazoles, the inventors filed Japanese Patent Applications No. 51515/1993 and No. 51516/1993 and the corresponding U.S. patent application (U.S. application Ser. No. 08/125,220).

However, this process comprising halogenating an 2-alkyl-5-formylimidazole with an N-halosuccinimide entails the by-production of the 2-alkyl-4,5-dihaloimidazole to detract from the yield of the object compound. This necessitates a purification step but the inventors' investigation revealed that the above by-product could not be sufficiently removed by the usual purification procedures such as recrystallization from a solvent, pH fractional crystallization, active carbon treatment, etc.

The object of this invention is, therefore, to provide a commercially useful purification method for 2-alkyl-4-halo-5-formylimidazoles, by which the impurity 2-alkyl-4,5-dihaloimidazoles can be efficiently removed.

SUMMARY OF THE INVENTION

The method of purifying an 2-alkyl-4-halo-5-formylimidazole according to this invention comprises dissolving the 2-alkyl-4-halo-5-formylimidazole containing the corresponding 2-alkyl-4,5-dihaloimidazole as an impurity in an aqueous solution of a sulfonating agent and adjusting the solution to pH 1–6 to thereby provide an aqueous solution containing the sulfonyl compound and then removing the water-insoluble impurity by filtration or extraction. This process is hereinafter referred to as purification process 1.

Preferably, this purification process 1 is followed by a second purification process (hereinafter referred to as purification process 2) which comprises adjusting the filtrate or extraction residue aqueous layer to pH 6.5–8.2 with an alkali and removing the precipitated impurity by filtration or extraction.

After the above purification process 1 or purification process 2, the object compound is isolated by adjusting the filtrate or extraction residue aqueous layer to pH 8.4–11 with an alkali.

DETAILED DESCRIPTION OF THE INVENTION

The compound to be purified by the method of this invention, that is an 2-alkyl-4-halo-5-formylimidazole, is produced from the corresponding 2-alkyl-5-hydroxymethylimidazole by the method described hereinafter.

<2-Alkyl-5-hydroxymethylimidazole>

A 2-alkyl-5-hydroxymethylimidazole can be synthesized, for example by reacting hydroxymethylglyoxal, a monoaldehyde and ammonia in a sequence such that the monoaldehyde and ammonia are first reacted with each other and hydroxymethylglyoxal is then introduced into the reaction system for further reaction.

The monoaldehyde can be an aliphatic aldehyde such as acetaldehyde, propionaldehyde, valeraldehyde, n-butyraldehyde, etc. or an aromatic aldehyde such as benzaldehyde.

For this reaction, the preferred molar ratio of hydroxymethylglyoxal, monoaldehyde and ammonia is 1.0/1.0-2.0/2.0-3.0. This reaction is conducted in an aqueous medium, but an organic solvent may be used in a small proportion in combination with water.

In conducting the reaction, the monoaldehyde and ammonia are first introduced into the aqueous medium for reaction. Typically, ammonia is first introduced (aqueous ammonia) and, then, the monoaldehyde is added dropwise or en bloc.

The monoaldehyde can be used as it is but in order to improve its solubility in aqueous medium, it is more advantageous to use a solution of the monoaldehyde in an organic solvent such as methanol or ethanol.

The reaction temperature may be about 10° to 60° C. and is preferably about 20° to 40° C. The reaction time is preferably in the range of about 1.0 to 5.0 hours. Thereafter, hydroxymethylglyoxal is introduced into the system and the reaction is further continued. While this reactant can be added en bloc, it is preferably added dropwise.

The reaction temperature in this stage may be about 10° to 60° C. and is preferably 20 to 40° C. The reaction time may practically range from about 1.0 to 5.0 hours. After completion of charging, the reaction system is ripened for about 0.5 to 2.0 hours to complete the reaction. The object compound is then isolated from the reaction mixture by the per se known procedure such as extraction.

Aside from the above process involving hydroxymethylglyoxal, monoaldehyde and ammonia, the process of reacting an amidine salt, such as valeroamidine hydrochloride, dihydroxyacetone and ammonia to give the 2-alkyl-5-hydroxymethylimidazole can also be employed with advantage.

<Crude 2-alkyl-4-halo-5-formylimidazole>

The object compound 2-alkyl-4-halo-5-formylimidazole can be synthesized from the above starting compound 2-alkyl-5-hydroxymethylimidazole by oxidizing the latter to the corresponding 2-alkyl-5-formylimidazole and halogenating this 2-alkyl-5-formylimidazole with an N-halosuccinimide (NHSI). This synthetic route can be schematically shown below.

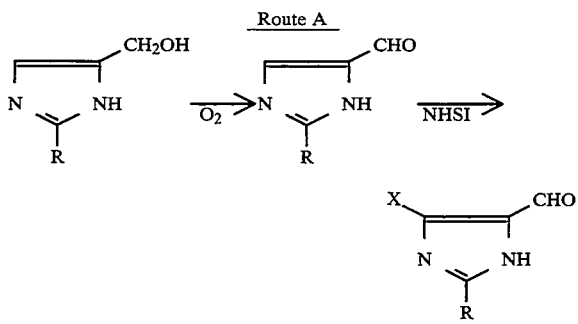

Route A

The object compound 2-alkyl-4-halo-5-formylimidazole can also be obtained by halogenating the corresponding 2-alkyl-5-hydroxymethylimidazole with an N-halosuccinimide (NHSI) and then oxidizing the halogenated compound. This synthetic route is schematically shown below.

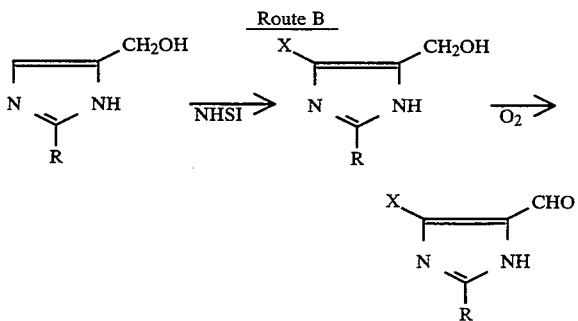

Route B

The alkyl group of the starting compound 2-alkyl-5-hydroxymethylimidazole is an alkyl group of 2–6 carbon atoms and the halogen of said N-halosuccinimide is either chlorine or bromine. The product 2-alkyl-4-halo-5-formylimidazole corresponds to the species of alkyl and halogen employed.

Route A is first described.

Oxidation Reaction

The production of 2-alkyl-5-formylimidazole by oxidation of 2-alkyl-5-hydroxymethylimidazole is preferably carried out as follows.

This oxidation reaction is conducted in the presence of a noble metal catalyst. As the noble metal catalyst, there may be employed a noble metal (inclusive of the metallic form as well as the form of a salt, oxide or the like) selected from the group consisting of platinum, palladium and gold. In particular, platinum and palladium are suited for practical use. These noble metals may be used in combination with bismuth, cerium, lead, indium or the like as a second component.

The noble metal catalyst is used as such or, when necessary, in the form supported on a carrier such as active carbon, silica or alumina.

The catalytic oxidation in the presence of such a noble metal catalyst is carried out in an appropriate solvent. Generally, the solvent is used in an amount of 3 to 50 parts by weight per part by weight of the starting material.

The solvent to be used includes, among others, lower carboxylic acids (e.g. acetic acid, propionic acid, etc.) or aqueous lower carboxylic acids, alcohols (e.g. tert-butanol etc.) or aqueous alcohols, ketones (e.g. acetone, methyl ethyl ketone, etc.) or aqueous ketones, ethers (e.g. dioxane, tetrahydrofuran, etc.) or aqueous ethers, and carboxylic acid esters (e.g. methyl acetate, ethyl acetate, etc.) or aqueous carboxylic acid esters. It is advantageous to use aqueous (water-containing) solvents from the product yield viewpoint in the case of lower carboxylic acids and from the product recovery viewpoint in the case of other solvents. In this case, it is practical that the water content be 1 to 70% by weight, preferably 10 to 60% by weight. Hereinafter, these solvents are referred to as "group 1 solvents."

For achieving a further improved product yield, it is particularly desirable that catalytic oxidation in the presence of the noble metal catalyst mentioned above be performed in an aqueous alkali (i). It is also desirable that said oxidation be carried out in a mixed solvent (ii) composed of an aqueous alkali and an organic solvent immiscible with water. Hereinafter, solvents of the type (i) are referred to as "group 2 solvents" and solvents of the type (ii) as "group 3 solvents."

As the alkali to be used in the group 2 and group 3 solvents, there may be mentioned sodium hydroxide, potassium hydroxide, sodium carbonate, potassium carbonate and sodium acetate, among others.

As the organic solvent immiscible with water in the group 3 solvents, there may be mentioned ketones, such as methyl isobutyl ketone etc., esters, such as ethyl acetate etc., halogenated hydrocarbons, such as ethylene dichloride etc., aromatic hydrocarbons, such as toluene etc., and aliphatic hydrocarbons, such as cyclohexane etc., among others.

From the practical use viewpoint, the proportions of the organic solvent immiscible with water and the aqueous alkali in the group 3 solvents are within the range of 1:100 to 100:1, preferably 10:1 to 1:10.

When an aqueous alkali (group 2 solvent) is used as the solvent, the alkali should be used in an amount of not less than 0.9 mole, preferably 1.0 to 1.5 moles, per mole of the starting material hydroxymethylimidazole. If the amount of the alkali is less than 0.9 mole, the product formylimidazole will not be dissolved in the system.

When a mixed solvent (type 3 solvent) composed of an organic solvent immiscible with water and an aqueous alkali is used as the solvent, the alkali is used desirably in an amount of not less than 0.01 mole, preferably 0.05 to 0.8 mole, per mole of the starting material 2-alkyl-5-hydroxymethyl imidazole.

When group 1 solvents are used, the catalyst is used suitably in an amount of 0.1 to 50 mole percent, preferably 1 to 20 mole percent, on the noble metal basis, per mole of the starting material 2-alkyl-5hydroxymethylimidazole.

When group 2 or group 3 solvents are used, the catalyst is used suitably in an amount of 0.01 to 50 mole percent, preferably 0.1 to 20 mole percent, on the noble metal basis, per mole of the starting material hydroxymethylimidazole.

In carrying out the catalytic oxidation, the reactor is charged with one of the solvents mentioned above, and the catalyst and the starting material hydroxymethylimidazole are fed to the reactor.

When a group 1 solvent is used as the solvent, the reaction temperature is suitably not lower than 50° C., preferably 60° to 170° C., and the reaction time is suitably within the range of 3 to 24 hours, preferably 5 to 15 hours.

When a group 2 or group 3 solvent is used as the solvent, the reaction temperature may be within the range of 0° C. to the refluxing temperature but is suitably not lower than room temperature, preferably 20° to 80° C., and the reaction time is suitably within the range of 1 to 24 hours, preferably 2 to 15 hours.

For effecting the catalytic oxidation reaction, oxygen or air is introduced into the reaction system. The system may be under atmospheric pressure or under increased pressure. Introduction of oxygen or air is carried out at a rate of about 0.1 to 10 liters per minute per liter of the liquid reaction mixture. When no more oxygen absorption is observable, the reaction is discontinued and the catalyst is removed from the reaction mixture by filtration.

When a group 1 solvent is used, the filtrate is concentrated under reduced pressure and crystals of the 2-alkyl-5-formylimidazole are collected and, if necessary, subjected to further purification.

When a group 2 solvent is used, the product 2-alkyl-5-formylimidazole is found dissolved in the filtrate in the form of a salt and, therefore, the filtrate is neutralized with an inorganic acid, such as sulfuric acid or hydrochloric acid, and crystals of the product 2-alkyl-5-formylimidazole are collected and, if necessary, subjected to further purification.

When a group 3 solvent is used, the filtrate is neutralized with an acid and then allowed to separate into two layers, the aqueous layer is separated, the organic layer is concentrated under reduced pressure and crystals of the product 2-alkyl-5-formylimidazole are collected and, if necessary, subjected to further purification.

Halogenation Reaction

Halogenation of the 2-alkyl-5-formylimidazole with an N-halosuccinimide is carried out by adding 0.5-1.5 moles, preferably 0.7-1.15 moles, of the N-halosuccinimide to each mole of the 2-alkyl-5-formylimidazole and allowing them to react in the absence of a catalyst or in the presence of a catalyst.

The solvent which can be used for this reaction includes various organic solvents, e.g. halogenated hydrocarbons such as methyl chloride, chloroform, carbon tetrachloride, 1-chloroethane, 1,2-dichloroethane, etc., saturated hydrocarbons such as pentane, hexane, heptane, octane, etc., aromatic hydrocarbons such as benzene etc., esters such as ethyl acetate, isopropyl acetate, etc. and ethers such as diethyl ether, dipropyl ether, dioxane, tetrahydrofuran, etc. These solvents may be used alone or in combination.

The amount of the solvent is, as a rule, not critical if it does not exceed the solubility limit of the particular 2-alkyl-5-formylimidazole in that solvent but for all practical purposes is within the range of 5 to 20 parts by weight relative to the 2-alkyl-5-formylimidazole.

The reaction temperature is generally 0°-150° C. and preferably 30°-100° C. The reaction time is 0.5-7 hours and preferably 1-3 hours.

After completion of the reaction, the reaction mixture is concentrated under reduced pressure and water and an aqueous solution of mineral acid such as hydrochloric acid for removing the impurity are added to the residue. For further yield enhancement, a salt such as sodium chloride is added and the precipitate is recovered by filtration or extracted into ethyl acetate or the like. In this manner, crude 2-alkyl-4-halo-5formylimidazole is obtained.

Route B, which is the reversal of Route A in the order of oxidation and halogenation, can be carried out under the same conditions as described above.

<Purification>

This crude 2-alkyl-4-halo-5-formylimidazole contains a substantial amount of 2-alkyl-4,5-dihaloimidazole and is, therefore, subjected to purification.

The purification stage consists of two processes, namely purification process 1 and purification process 2. However, since a fairly satisfactory degree of purification can be achieved by purification process 1 alone, purification process 2 is carried out only if a still higher purity is desired.

Purification Process 1

In this process, the crude 2-alkyl-4-halo-5formylimidazole mentioned above is first added to an aqueous solution of a sulfonating agent and the mixture is adjusted to pH 1-6, preferably pH 1.5-6 and, for still better results, pH 1.5-5 to prepare an aqueous solution of the sulfonation product. Then, the water-insoluble impurity is removed by filtration or extraction. In this step, activated carbon is preferably added for decolorization and further elimination of the byproduct and impurity.

The sulfonating agent that can be used includes sodium hydrosulfite, potassium hydrosulifite, sodium sulfite, potassium sulfite and sulfur dioxide, among others. The amount of the sulfonating agent, based on each mole of 2-alkyl-4-halo-5-formylimidazole, is 0.8 to 5 moles and preferably 1 to 2.5 moles.

This procedure is carried out at room temperature through the boiling point of the solvent and preferably at 50°-80° C. The dissolution time of the sulfonation production is about 10 minutes to about 5 hours.

The pH control agent which can be used for pH adjustment in this process includes inorganic acids such as hydrochloric acid, sulfuric acid, phosphoric acid, etc. and organic acids such as acetic acid, propionic acid, lactic acid, oxalic acid, etc. In certain instances, metal hydroxides such as sodium hydroxide, potassium hydroxide, etc., ammonia, amines and salts such as sodium dihydrogen phosphate, sodium phosphate, sodium carbonate, etc. can also be employed.

The extraction solvent which can used in the above process includes benzene, toluene, 1,2-dichloroethane, chloroform, ethyl acetate, propyl acetate, methyl ethyl ketone, methyl isobutyl ketone and so on.

Purification Process 2

If further purification is required, the filtrate or extraction residue aqueous layer obtained in the above purification process 1 is adjusted to pH 6.5-8.2, preferably pH 6.5-8, with an alkali and the precipitated impurity is then removed by filtration or extraction.

Precipitation of the impurity will not be thorough if the pH of the system is less than 6.5, while much of 2-alkyl-4-halo-5-formylimidazole will also be precipitated if the pH is higher than 8.2. Therefore, such conditions should be avoided.

The alkali mentioned above includes metal hydroxides such as sodium hydroxide, potassium hydroxide, calcium hydroxide, etc., ammonia, amines and salts such as sodium monohydrogen phosphate, sodium phosphate, sodium carbonate, sodium hydrogen carbonate, potassium hydrogen carbonate, etc.

The extracting solvent which can be used includes the species mentioned hereinbefore.

By following the above purification process 2, the desired 2-alkyl-4-halo-5-formylimidazole of still higher purity can be obtained.

<Isolation of the object compound>

The filtrate or extraction residue obtained in purification process 1 or purification process 2 is adjusted to pH 8.4–11, preferably pH 8.5–10, with an alkali to precipitate the 2-alkyl-4-halo-5-formylimidazole, which is then isolated by filtration or extraction to provide the object product. When the pH is below 8.4, the precipitation of 2-alkyl-4-halo-5-formylimidazole is not thorough. On the other hand, when the pH exceeds 11, the 2-alkyl-4-halo-5-formylimidazole tends to be decomposed. The addition of a salt soluble in the solution, such as sodium chloride, in this procedure is recommendable because the precipitation yield of the object compound is increased by the salting-out effect.

The alkali for pH adjustment includes the species mentioned above. The extracting solvent may also be any of the species mentioned hereinbefore.

Thus, in accordance with the purification method of this invention, the major impurity 2-alkyl-4,5-dihaloimidazole is effectively removed and, at the same time, other impurities are also eliminated so that an 2-alkyl-4-halo-5-formylimidazole of extremely high purity can be obtained.

EXAMPLES

The following examples are intended to illustrate this invention in further detail.

Reference Example 1

<Production of 2-butyl-4-chloro-5-formylimidazole>

To 15.2 kg of dioxane were added 800 g (5.26 moles) of 2-butyl-5-formylimidazole and 562 g (4.21 moles) of N-chlorosuccinimide and the reaction was carried out with stirring at a constant temperature of 70° C. for 1.0 hour. The reaction mixture was then ripened for 0.5 hour and concentrated under reduced pressure to provide 1440 g of brown concentrate. To this concentrate was added 960 g of 10 wt. % hydrochloric acid and the mixture was stirred at 50° C. for 2 hours. After cooling to room temperature, 920 g of water and 3080 g of 10 wt. % aqueous sodium chloride were added and the mixture was extracted with 7.1 l of ethyl acetate. After phase separation, the aqueous layer was further extracted with 4.5 l of ethyl acetate. The ethyl acetate layers were combined, washed with 1.0 l of water and the ethyl acetate was distilled off under reduced pressure to recover 596 g of brown liquid. This brown liquid crystallized on spontaneous cooling. The crystals thus obtained were dried in vacuo at room temperature overnight to give 396 g of brown crystals. Quantitative analysis of the crystalline product by high performance liquid chromatography revealed that it contained 372 g of 2-butyl-4-chloro-5-formylimidazole and 15 g of 2-butyl-4,5-dichloroimidazole. The purity of the end product was 94%.

EXAMPLE 1

To 20.00 g of the brown crystalline product obtained in Reference Example 1 (containing 18.8 g of 2-butyl-4-chloro-5-formylimidazole and 0.76 g of 2-butyl-4,5-dichloroimidazole) was added 418 g of 6.0 wt. % aqueous sodium hydrosulfite and the mixture was adjusted to pH 3.4 with 6.4 g of acetic acid and stirred at 60° C. for 2 hours.

After the mixture had cooled to 30° C., the insoluble matter was filtered off, 2.0 g of 50 wt. % hydrous activated carbon was added to the filtrate, and the mixture was stirred for 30 minutes. The activated carbon was then filtered off and the filtrate was adjusted to pH 9.0 with 28.4 g of 48.8 wt. % aqueous sodium hydroxide. Then, 60 g of sodium chloride was added and the mixture was further stirred for 30 minutes. The resultant crystals were collected by filtration, rinsed well and dried to recover 17.10 g of light-yellow crystals. Analysis of this crystalline product by high performance liquid chromatography revealed that it contained 17.02 g of 2-butyl-4-chloro-5-formylimidazole and 0.02 g of 2-butyl-4,5-dichloroimidazole. The purity of the object compound was 99.5%.

EXAMPLE 2

To 5.00 g of the brown crystals obtained in Reference Example 1 (containing 4.70 g of 2-butyl-4-chloro-5-formylimidazole and 0.19 g of 2-butyl-4,5-dichloroimidazole) was added 260 g of 4.9 wt. % aqueous sodium hydrosulfite and the mixture was stirred at 50° C. for 20 minutes. Then, 100 ml of 1,2-dichloroethane was added (pH 3.5) and after 5 minutes' stirring, the 1,2-dichloroethane solution (bottom layer) was separated.

The aqueous layer was adjusted to pH 8.5 with sodium hydrogen carbonate and extracted with three 100 ml portions of 1,2-dichloroethane. These 1,2-dichloroethane layers were pooled, washed with 200 ml of water, concentrated under reduced pressure and dried to provide 3.06 g of yellow crystals. HPLC analysis of this crystalline product revealed that it contained 3.03 g of 2-butyl-4-chloro-5-formylimidazole and 0.02 g of 2-butyl-4,5-dichloroimidazole. The purity of the object compound was 99.3%.

EXAMPLE 3

To 21.00 g of the brown crystals obtained in Reference Example 1 (containing 18.93 g of 2-butyl-4-chloro-5-formylimidazole and 1.92 g of 2-butyl-4,5-dichloroimidazole) was added 418 g of aqueous sodium hydrosulfite and the mixture was adjusted to pH 3.0 with 16.73 g of sodium dihydrogen phosphate dihydrate and 2.77 g of 85 wt. % phosphoric acid. Then, 2.3 g of 50 wt. % hydrous active carbon was added and the mixture was stirred at 60° C. for 3 hours.

After cooling to 30° C., the insoluble matter was filtered off and the filtrate was adjusted to pH 9.0 with 35.21 g of 40 wt. % aqueous potassium hydroxide for crystallization. To this slurry was added 60 g of sodium chloride and the mixture was stirred for 30 minutes. The resultant crystals were recovered by filtration, rinsed well and dried to provide 17.42 g of white crystals. HPLC analysis of this crystalline product revealed that it contained 17.33 g of 2-butyl-4-chloro-5-formylimidazole and 0.03 g of 2-butyl-4,5-dichloroimidazole. The purity of the object compound was 99.5%.

EXAMPLE 4

The procedure described in Example 1 was repeated except that 420 g of 6 wt. % aqueous sodium sulfite was used in lieu of 6.0 wt. % aqueous sodium hydrosulfite to provide 14.55 g of light-yellow crystals. HPLC analysis of this crystalline product revealed that it contained 14.51 g of 2-butyl-4-chloro-5-formylimidazole and 0.02 g of 2-butyl-4,5-dichloroimidazole. The purity of the object compound was 99.7%.

EXAMPLE 5

The procedure of Example 1 was repeated except that the sulfonation product was prepared by using 425 g of 3 wt. % aqueous sulfurous acid in lieu of 6.0 wt. % aqueous sodium hydrosulfite and adjusting the system to pH 3.5 with 40 wt. % aqueous sodium hydroxide to provide 17.10 g of light-yellow crystals. HPLC analysis of this crystalline product revealed that it contained 17.02 g of 2-butyl-4-chloro-5-formylimidazole and 0.02 g of 2-butyl-4,5-dichloroimidazole. The purity of the object compound was 99.5%.

Reference Example 2

<Production of 2-propyl-4-chloro-5-formylimidazole>

Using 69.1 g (0.50 mole) of 2-propyl-5-formylimidazole and 53.4 g (0.40 mole) of N-chlorosuccinimide in 13.8 kg of dioxane, the procedure of Reference 1 was otherwise repeated to provide 35.6 g of light-yellow powder. HPLC analysis of this powder revealed that it contained 32.1 g of 2-propyl-4-chloro-5-formylimidazole and 3.3 g of 2-propyl-4,5-dichloroimidazole.

EXAMPLE 6

To 20.0 g of the light-yellow powder obtained in Reference Example 2 (containing 18.0 g of 2-propyl-5formylimidazole and 1.9 g of 2-propyl-4,5-dichlroimidazole) was added 380 g of 5 wt. % aqueous sodium hydrosulfite and the mixture was adjusted to pH 3.0 with 1.8 g of 50 wt. % sulfuric acid. This mixture was stirred at 60° C. for 30 minutes. The pH of the resulting slurry was 4.2. The slurry was adjusted again to pH 3.0 with 50 wt. % sulfuric acid and stirred at 60° C. for an additional 2 hours.

The insoluble matter was filtered off and 2.0 g of 50 wt. % hydrous active carbon was added. The mixture was stirred and allowed cool to room temperature in 40 minutes and the carbon was filtered off. The filtrate was adjusted to pH 9.1 with 40 wt. % aqueous sodium hydroxide and after 34 g of sodium chloride was added, the mixture was stirred for 30 minutes. The mixture was then cooled to 10° C. and the crystals were filtered. The filter cake was washed with 30 ml of cold water and dried to give 16.64 g of pale yellow crystals. HPLC analysis of this crystalline product revealed that it contained 16.60 g of 2-propyl-4-chloro-5-formylimidazole and 0.02 g of 2-propyl-4,5-dichloroimidazole, the purity of the object compound was 99.7%.

EXAMPLE 7

To 3.80 kg of dioxane were added 200 g (1.30 moles) of 2-butyl-5-formylimidazole and 139 g (1.04 moles) of N-chlorosuccinimide and the reaction was carried out with stirring at 70° C. for 1.5 hours. The reaction mixture was then concentrated under reduced pressure to give 363 g of brown concentrate. To this concentrate was added 356 g of 10 wt. % hydrochloric acid and the mixture was stirred at 50° C. for 2.5 hours. After cooling to room temperature, 1.79 kg of 15 wt. % aqueous sodium chloride was added. Then, 40 wt. % aqueous sodium hydroxide was added to adjust the pH to 2.0 and the resultant crystals were recovered by filtration. The filter cake was rinsed well and dried to provide 104.0 g of light-yellow powder. HPLC analysis of this crystalline powder revealed that it contained 92.2 g of 2-butyl-4-chloro-5-formylimidazole and 11.2 g of 2-butyl-4,5-dichloroimidazole.

To 21.3 g of the above crystals (containing 18.9 g of 2-butyl-4-chloro-5-formylimidazole and 2.30 g of 2-butyl-4,5-dichloroimidazole) was added 418 g of 6.0 wt. % aqueous sodium hydrosulfite and the mixture was adjusted to pH 3.47 with 6.3 g of acetic acid and stirred at 60° C. for 3 hours.

The insoluble matter was then filtered off and 2.0 g of 50 wt. % hydrous active carbon was added to the filtrate. The mixture was stirred and allowed to cool to room temperature in 45 minutes. The active carbon was then filtered off and 48.8 wt. % aqueous sodium hydroxide was added gradually to the filtrate for crystallization. When 19.8 g of aqueous NaOH had been added, a small amount of crystals separated out and, therefore, the addition of NaOH was terminated. The pH of the mixture at this time was 7.55. The mixture was further stirred for 15 minutes, at the end of which time the crystals were separated by filtration.

The filtrate was adjusted to pH 9.01 with 40 wt. % aqueous NaOH. Then, 60 g of sodium chloride was added and the mixture was stirred for 15 minutes. The resultant crystals were collected by filtration. The filter cake was rinsed with a small quantity of water and dried to provide 16.0 g of crystals. HPLC analysis of this crystalline product showed that it was 100% 2-butyl-4chloro-5-formylimidazole, not containing 2-butyl-4,5-dichloroimidazole.

EXAMPLE 8

In the procedure of Example 7, the system was adjusted to pH 3.0 with 2.8 g of 85 wt. % phosphoric acid instead of using acetic acid. After the hydrous activated carbon was filtered off, 40 wt. % aqueous sodium hydroxide was gradually added to the filtrate until crystals separated out. When 23.3 g had been added, a small amount of crystals separated out and, therefore, the addition of NaOH was terminated. The pH of the mixture at this time was 7.53. The mixture was further stirred for 10 minutes, after which the crystals were filtered.

The filtrate was adjusted to pH 9.02 with 40 wt. % sodium hydroxide and the mixture was stirred for 20 minutes. The resultant crystals were recovered by filtration. The filter cake was rinsed with a small quantity of water and dried to give 14.3 g of crystals. HPLC analysis of this crystalline product revealed that it was 100% 2-butyl-4-chloro-5-formylimidazole, not containing 2-butyl-4,5-dichloroimidazole.

EXAMPLE 9

To 1380 g of dioxane were added 69.1 g (0.50 mole) of 2-propyl-5-formylimidazole and 53.4 g (0.40 mole) of N-chlorosuccinimide and the reaction was carried out at 70° C. for 1.5 hours. The reaction mixture was then concentrated under reduced pressure to give 133 g of brown concentrate. To this concentrate was added 146 g of 10 wt. % hydrochloric acid and the mixture was stirred at 50° C. for 2.5 hours, after which 190 g of 20 wt. % aqueous sodium chloride was added. The mixture was adjusted to pH 2.0 with 40 wt. % aqueous NaOH, followed by cooling to 10° C. The resultant crystals were separated by filtration and the filter cake was rinsed thoroughly and dried to provide 35.3 g of light-yellow powder. HPLC analysis of this powder revealed that it contained 31.8 g of 2-propyl-4-chloro-5-formylimidazole and 3.3 g of 2-propyl-4,5-dichloroimidazole.

To 19.4 g of the above crystalline powder (containing 17.5 g of 2-propyl-4-chloro-5-formylimidazole and 1.82 g of 2-propyl-4,5-dichloroimidazole) was added 418 g of 5.0 wt. % aqueous sodium hydrosulfite and the mixture was adjusted to pH 2.0 with 50 wt. % sulfuric acid and stirred at 60° C. for 2 hours.

The insoluble matter was filtered off, 2.3 g of 50 wt. % hydrous activated carbon was added to the filtrate and the mixture was stirred for 45 minutes while it was allowed to cool to room temperature. The activated carbon was filtered off and 40 wt. % aqueous sodium hydroxide was gradually added until crystals separated out. When 25.8 g had been added, a small amount of crystals separated out and, therefore, the addition of NaOH was terminated. The pH of the mixture at this time was 7.74. The mixture was further stirred for 15 minutes, at the end of which time the crystals were separated by filtration.

The filtrate was adjusted to pH 9.05 with 40 wt. % aqueous sodium hydroxide and after 60 g of sodium chloride was added, the mixture was stirred for 15 minutes and the resultant crystals were separated by filtration. The filter cake was washed with a small quantity of cold water and dried to give 14.6 g of crystals. HPLC analysis of this crystalline product revealed that it was 100% 2-propyl-4-chloro-5-formylimidazole, not containing 2-propyl-4,5-dichloroimidazole.

Reference Example 3

<Production of 2-butyl-4-chloro-5-hydroxymethylimidazole>

To 210 g of ethyl acetate were added 15.4 g of 2-butyl-5-hydroxymethylimidazole and 14.7 g of N-chlorosuccinimide and the reaction was carried out with stirring at 20° C. for 3 hours.

The reaction mixture was then concentrated under reduced pressure to remove 120 g of ethyl acetate. The crystals obtained by filtration were rinsed with 100 ml of water and dried to give 11.9 g of crystals. Quantitative analysis of this crystalline product by HPLC revealed that it contained 2.5% of 2-butyl-4,5-dichloroimidazole. The purity of the object compound was 96.5%.

<Synthesis of 2-butyl-4-chloro-5-formylimidazole>

To 100 ml of 2.5% aqueous NaOH solution was added 10 g of the 2-butyl-4-chloro-5-hydroxymethylimidazole obtained in Reference Example 3. To this mixture was added 2.7 g of a platinum-bismuth catalyst (5% Pt and 2% Bi on active charcoal, water content 50%) and oxygen was bubbled through the system at the rate of 80 ml/minute under stirring at room temperature for 2.5 hours for oxidation.

After this oxidation reaction, the catalyst was filtered off and the filtrate was neutralized with 20% aqueous $NaSO_4$ and dried to give 9.4 g of crystals. Quantitative analysis of this crystalline product by HPLC revealed that it contained 2.3% of 2-butyl-4,5dichloroimidazole. The purity of the object compound was 97.0%.

EXAMPLE 10

Using the crystals obtained in Reference Example 3, the procedure of Example 1 was otherwise repeated. The purity of the object compound was 99.5%.

What is claimed is:

1. A method of purifying a 2-alkyl-4-halo-5-formylimidazole which comprises dissolving a 2-alkyl-4-halo-5-formylimidazole containing the corresponding 2-alkyl-4,5-dihaloimidazole as an impurity in an aqueous solution of a sulfonating agent and adjusting the solution to pH 1-6 to thereby provide an aqueous solution of the sulfonation product and then removing the water-insoluble impurity by filtration or extraction.

2. The purification method according to claim 1 further comprising a step of adjusting the resultant filtrate or extraction residue aqueous layer to pH 8.4–11 with an alkali to thereby isolate the 2-alkyl-4-halo-5-formylimidazole.

3. A method of purifying a 2-alkyl-4-halo-5-formylimidazole which comprises dissolving a 2-alkyl-4-halo-5-formylimidazole containing the corresponding 2-alkyl-4,5-dihaloimidazole as an impurity in an aqueous solution of a sulfonating agent, adjusting the solution to pH 1-6 to thereby provide an aqueous solution of the sulfonation product, then removing the water-insoluble impurity by filtration or extraction, adjusting the resultant filtrate or extraction residue aqueous layer to pH 6.5–8.2 with an alkali and removing additional precipitated impurity by filtration or extraction.

4. The purification method according to claim 3 further comprising a step of adjusting the filtrate or extraction residue aqueous layer at pH 6.5–8.2 to pH 8.4–11 with an alkali to thereby isolate the 2-alkyl-4-halo-5-formylimidazole.

* * * * *